United States Patent [19]

Kenkare et al.

[11] 4,411,883

[45] Oct. 25, 1983

[54] ANTIPERSPIRANT

[75] Inventors: Divaker B. Kenkare, South Plainfield; Durland K. Shumway, Piscataway, both of N.J.

[73] Assignee: Colgate-Palmolive Company, New York, N.Y.

[21] Appl. No.: 584,324

[22] Filed: Jun. 6, 1975

Related U.S. Application Data

[63] Continuation-in-part of Ser. No. 329,429, Feb. 5, 1973, abandoned.

[51] Int. Cl.$^3$ .......................... A61K 7/34; A61K 9/00
[52] U.S. Cl. ........................................ 424/47; 424/65; 424/66; 424/67; 424/68
[58] Field of Search ..................................... 424/47, 68

[56] References Cited

U.S. PATENT DOCUMENTS

| | | | |
|---|---|---|---|
| 2,736,683 | 2/1956 | Apperson et al. | 424/68 |
| 2,765,213 | 10/1956 | Beekman | 424/68 X |
| 3,014,844 | 12/1961 | Thiel et al. | 424/46 |
| 3,211,620 | 10/1965 | Henkin et al. | 424/68 |
| 3,288,681 | 11/1966 | Goldberg | 424/47 |
| 3,325,367 | 6/1967 | Miechowski et al. | 424/68 X |
| 3,493,509 | 2/1970 | Messina | 252/51.5 A |
| 3,928,557 | 12/1975 | Wright et al. | 424/47 |

FOREIGN PATENT DOCUMENTS

| | | | |
|---|---|---|---|
| 687228 | 1/1967 | Belgium | 424/68 |
| 1553235 | 12/1968 | France | 252/51.5 |
| 987301 | 3/1965 | United Kingdom | 424/68 |
| 1111867 | 5/1968 | United Kingdom | 424/68 |
| 1167173 | 10/1969 | United Kingdom | 424/68 |

*Primary Examiner*—Dale R. Ore
*Attorney, Agent, or Firm*—Herbert S. Sylvester; Murray M. Grill; Norman Blumenkopf

[57] ABSTRACT

A dry aerosol antiperspirant composition containing an astringent powder, an aerosol propellant, and a di($C_{8-10}$ alkanoate) of a $C_{2-6}$ alkylene diol such as propylene dipelargonate, and method of using same.

10 Claims, No Drawings

ANTIPERSPIRANT

This application is a continuation-in-part of our co-pending application Ser. No. 329,429 filed Feb. 5, 1973 now abandoned which application is a continuation of our application Ser. No. 89,499 filed Nov. 13, 1970 and now abandoned.

This invention relates to stable aerosol antiperspirant formulations containing an antiperspirant salt such as aluminum sulfamate or aluminum chlorhydrate as the effective sweat inhibitor and a lower alkylene dialkanoate carrier for said salt.

Antiperspirant formulations have heretofore been made in the form of creams, lotions, powders, sticks, pads, sprays and the like. In recent years, the aerosol system has been developed wherein an aerosol composition is pressurized by a liquidfied gaseous propellant and packaged in a suitable container, such as a metal bomb. The most effective antiperspirant compounds utilized are the water soluble aluminum salts such as aluminum sulfate, aluminum chloride, aluminum chlorhydrate and the like in aqueous solution. However, water-containing aerosol antiperspirant formulations have been the cause of numerous problems inclusive of the corrosive action of the soluble aluminum salt, clogging of the valve of the container, dripping of the spray caused by too wet a spray, instability of the formulation whereby a separation of the phases occur.

Attempts to exclude water from the aerosol formulation by incorporating the powdered salt in such form that it is dispensed from the aerosol container as a powder also have proven to be disadvantageous in various respects. This is so because the astringent salt is expelled from the dispenser as a slow settling cloud of fine dust which, because of the proximity of the axilla to the face, may be inhaled by the user.

Some of the foregoing disadvantages have been minimized by employing aerosol formulations which contain a dispersion or suspension of the powdered astringent antiperspirant salt in a liquid propellent in which there is present a non-volatile, nonhygroscopic liquid carrier-emollient, such as a lower alkyl ester of a long chain saturated fatty acid, e.g., isopropyl myristate, or an alkylene triol esterified with a long chain unsaturated fatty acid, e.g., glyceryl trioleate. While such formulations overcome the disadvantages of corrosion, valve clogging, and dust cloud formation by being anhydrous and by providing adherent sprays of the powdered astringent salt, the fatty acid ester diminishes antiperspirant activity and can deposit an unpleasant, oily-feeling film upon the skin. A composition of somewhat improved antiperspirant effect is obtained, according to German Pat. No. 2,137,926 by employing an anhydrous aerosol formulation in which a carrier-emollient of the composition is an alkyl ester of a polycarboxylic acid which contains a relatively high ratio, 0.125:1 to 0.214:1, of ester groups to carbon atoms. Such polyester-containing antiperspirant aerosol formulations also suffer from the disadvantage of producing an unpleasant oily-feeling film on application to the skin.

Applicants have elimanted the aforesaid problems by formulating a substantially anhydrous suspension of the antiperspirant compound in the form of a powder in an organic propellant containing a vehicle which is a lower alkylene dialkanoate. More particularly, the foregoing disadvantages of prior art dry aerosol perspiration inhibiting compositions are overcome by the provision according to the present invention of a novel dry aerosol astringent and antiperspirant composition comprising 0.2 to 12% by weight of an astringent powder which has a particle size of less than about 100 microns and which is suspended in from 0.3 to 50% by weight of an essentially anhydrous, saturated, lower alkylene dialkanoate wherein the alkanoate residues each contain from 8 to 10 carbon atoms, the weight ratio of astringent powder to alkylene dialkanoate being in the range of from about 0.1:1 to 3:1, and from 60 to 98% by weight of a liquid propellant selected from the group consisting of hydrocarbons, halogenated hydrocarbons, and mixtures thereof, which have a vapor pressure at 70° F. in the range of about 15 to 100 lbs./sq. in. gauge. The invention also includes an aerosol package consisting of a pressure-tight container having a valve-controlled opening containing the above described novel astringent antiperspirant composition.

The aerosol composition of the invention is of excellent antiperspirant effect and is dispensed in a fast settling initially liquid form. On application to the skin the novel composition also provides a smooth dry film which, in contrast to prior art aerosol antiperspirants, is characterized by a distinctly non-oily feeling.

In preferred embodiments of the invention the concentration of antiperspirant astringent powder in the present aerosol composition is 1 to 10% by weight, preferably 2.5 to 6% by weight, the concentration of the lower alkylene dialkanoate is preferably 0.3 to 12% by weight, especially 0.5 to 8%, and the concentration of liquid propellant is 70 to 96% by weight, preferably 80 to 94% by weight.

Another preferred additive to the instant formulation is a suspending agent which retards agglomeration of the particles, decreases the settling rate of the particles and increases the viscosity of the aerosol suspension such as colloidal silica. A product found particularly useful herein is "Cab-O-Sil" a colloidal silica available from Godfrey L. Cabot, Boston, Mass., which has a particle size below about 5 microns. Cab-O-Sil M-5 is a submicroscopic particulate silica prepared in a hot gas environment of about 1,100° C. by the vapor phase hydrolysis of silicon compound.

Other preferred suspending agents are the finely divided hydrophobically treated clays such as a reaction product of a clay such as bentonite or hectorite with, for example, dimethyldistearyl ammonium chloride. These suspending agents are the hydrophobically treated montmorillonite or hectorite clays available under the trademark "Bentone" which are prepared by reacting a clay such as bentonite or hectorite in a cation exchange system with a variety of amines. Different amines are reacted to obtain different Bentone suspending agents which may also differ in proportions of $SiO_2$, MGO and $Al_2O_3$. Examples of useful Bentone suspending agents are Bentone-27, which is stearaluminum hectorite, Bentone-34, which is quaternium 18 Bentonite, Bentone-38, which is quaternium 18 hectorite, and Bentone-14, which is a clay extended quaternium 18 hectorite, all of which have a particle size of below about 5 microns and are commercially available from the NL Industries, Inc.

The hydrophobic clays should be thoroughly dispersed. Three forms of energy which aid in such dispersion are temperature increase, chemical energy and mechanical shearing action. Chemical energy can be supplied in the form of a polar additive such as alcohol or a high boiling organic liquid such as propylene carbonate. Propylene carbonate, usually in an amount of about 0.05% to about 0.5%, is also particularly helpful when the organic liquid has poor wetting properties, or when dispersion is unusually difficult. As taught by NL Industries in their Data Sheet B-33 of April 1970, high mechanical shearing action is also an important factor. Equipment such as homogenizers, shear pumps, and colloid mills will give positive results. Examples of useful mixers include, among others, the Cowles Dissolver and the Eppenbach Homogenizer.

The suspending agent is employed in amounts of from about 0.05 to about 3%, desirably about 0.1 to 1%, and preferably from about 0.2 to about 0.7% thereof.

Any conventional liquified gaseous propellant or mixture of propellants may be used that has the requisite vapor pressure at atmospheric temperature to effectively disperse the aerosol composition from the spray container. That is to say, any non-toxic, volatile, organic material which exists as a gas at the temperature of use (and ambient or atmospheric pressure) and which exists as a liquid at the same temperature under superatmospheric pressures can be used as the gas-producing agent. Especially suitable are the $C_3$–$C_4$ aliphatic hydrocarbons, namely liquefied propane, n-butane, and isobutane; halogenated aliphatic hydrocarbons which contain from 1 to 2 carbon atoms and include, by way of example, methylene chloride, "Freons" such as dichlorodifluoromethane, monochlorodifluoromethane, dichlorotetrafluoroethane, trichlorofluoromethane, trichlorofluoroethane, difluoroethane, difluoromonochloroethane, trichlorotrifluoroethane, monofluorodichloromethane, monofluorodichloroethane, pentafluoromonochloroethane; cyclic hexafluorodichlorobutane; octafluoropropane; and cyclic octafluorobutane; and mixtures of two or more thereof. Preferably the saturated hydrocarbons and halogenated saturated aliphatic hydrocarbons are employed in the subject composition. The boiling point of said propellant, or of the mixture of propellants, used in the final product should fall within the range of about −30° C. to about 60° C. at atmospheric pressure. A highly desirable propellant for use in connection with the subject composition is a mixture of dichlorodifluoromethane and dichlorotetrafluoroethane in a 25:75 blend.

Although not essential for this invention, it is desirable to add a non-irritating, non-toxic germicide or bactericide in amounts of about 0.02 to .5% by weight of the total composition. Suitable antiseptic agents include dichlorophene, 3, 4′, 5 tribromosalicylanilide; 2, 2′, 3, 4-tetrabromosalicylanilide, and other bacteriostats commonly known in the market as well as mixtures thereof.

In addition to the foregoing components of the subject composition one may also include therein components such as perfumes, colorings, and the like, so as to improve the aesthetic value and consumer acceptability thereof. One may also incorporate talc or other powdered compounds to improve the properties of the product. Other compounds such as fatty amides, dipropylene glycol, antioxidants, lecithin, and/or vitamins, either separately or in combination may also be incorporated into the subject composition. Such compounds should not, however, be employed in quantities which impair the dry powder property of subject composition.

The powder which is employed as the antiperspirant and astringent agent according to the invention is any of the large number of pulverulent substances known for this function in the aerosol antiperspirant art. These are usually substantially insoluble in the aerosol composition (including propellant and carriers) and may be inactive in the dry state but in the presence of moisture are converted to an astringent, antiperspirant active form. Usually such antiperspirant compounds are acid salts of multivalent (di- or trivalent preferred) metal cations, typical examples of which include acid-reacting salts of aluminum, zirconium, zinc and iron, such as aluminum sulfamate, aluminum chlorohydrate, aluminum chloride, aluminum sulfate, aluminum oxychloride, aluminum oxysulfate, zirconium tetrachloride, zirconyl hydroxychloride, zirconyl oxychloride, ferric chloride, zinc sulfate and zinc sulfocarbolate. In addition to the foregoing astringent antiperspirant metal salts other known inorganic and organic salt mixtures and complex salts may be employed, such as the zirconium salt-amine and amino acid complexes of the type disclosed in U.S. Pat. No. 3,407,254; the zirconium salt-aluminum chlorhydroxide-glycol complexes of the type described in U.S. Pat. No. 3,405,153; the aluminum chlorohydroxide-glycol complexes of the type disclosed in U.S. Pat. No. 3,420,932; aluminum chlorohydroxide-zirconyl hydroxychloride-glycine complexes; zirconyl hydroxychloride-amino acid complexes; and zirconyl hydroxychloride-aluminum hydroxychloride complexes. Preferably the astringent acid salt is one containing aluminum, and aluminum sulfamate and aluminum chlorohydrate are especially preferred.

In accordance with normal practice in the dry aerosol antiperspirant art, the antiperspirant astringent agent is incorporated in the aerosol composition as an impalpable powder, i.e. a powder of particle size ranging from 1 to 100 microns, conveniently of an average particle size of about 10 to 25 microns. The powder is incorporated in the present composition in a non-solution, non-aqueous form, i.e. free of moisture other than very little chemically combined water.

The lower alkylene dialkanoate which is incorporatedin the present aerosol composition as an emollient carrier for the antiperspirant astringent powder is a non-hygroscopic, non-volatile liquid which provides a rapidly settling spray on application of the aerosol composition and promotes adherence of the antiperspirant to the user's skin. This constituent is the completely esterified derivative of a straight or branched chain glycol, i.e. a diol having 2 to 6 carbon atoms, such as ethylene glycol; 1,2-propylene glycol; 1,3-propylene glycol; 1,3-butylene glycol; 2,3-butylene glycol; 1,4-butylene glycol; 1,5-pentane diol; 1,6-hexane diol; 2,2-dimethyl-1,3-propane diol; and 2,2-dimethyl-1,3-butane diol, wherein the ester, i.e. alkanoate, residues are derived from the same or different straight or branched chain saturated fatty acids of 8 to 10 carbon atoms such as caprylic acid, i.e. octanoic acid, pelargonic acid, decanoic acid, 3,7-dimethyloctanoic acid and 2-ethylhexanoic acid. Representative examples of lower alkylene dialkanoates suitable for use as emollient-carriers in the present aerosol compositions include: ethylene-1,2-dioctanoate; ethylene-1-octanoate-2-pelargonate; ethylene-1,2-di-(2′-ethylhexanoate); propylene-1,2-dipelargonate; propylene-1,3-diperlargonate; butylene-1,3-didecanoate; butylene-2,3-dipelargonate; amylene-1,5-di-(3′,7′-dimethyloctanoate); hexane-1,6-didecanoate; 2,2-di-methylbutane-1,3-pelargonate; and 2,2-dimethylpropane-1-octanoate-3-(2′-ethylhexanoate). Mixtures of these and equivalent diesterified glycols can also be used. The present ester carrier emollients are characterized by a low ratio of ester groups to carbon atoms, i.e.

a ratio of ester groups to constituent carbon atoms of about 1:9 or less, preferably 1:9 to 1:11.

Preferably the lower alkylene dialkanoate is derived from a straight chain acid or acids and more preferably the aklylene residue thereof is derived from a straight chain glycol. Preferably the lower alkylene dialkanoate is a lower alkylene dipelargonate, especially a propylene dipelargonate. Such compounds, also referred to as propylene glycol dipelargonate, are either the 1,2- or 1,3-dipelargonates. They function even better than the other dialkanoates in aiding adherence of the antiperspirant powder to the skin, in settling the sprayed powder, in not interfering with the antiperspirant (after moistening) action of the astringent powder and in feeling non-oily and pleasant to the skin. Other dialkanoates which are of 2 or 4 carbon atoms per straight chain alkylene and are of about 9 carbon atoms per straight chain alkanoate are next preferred for the described properties.

The present aerosol antiperspirant compositions may be prepared according to conventional mixing and formulation techniques for the manufacture of dry aerosol antiperspirant compositions. Generally, the emollient-carrier ester and any dispersing agent are mixed together at room temperature and the pulverulent antiperspirant is added to the mixture. Mixing may be effected with a high shear mixer such as a Cowles Dissolver or other high speed blender. Any perfume, antibacterial compound or solvent to be used is then charged to the mixture which is subsequently introduced into an aerosol container of conventional design, i.e. a pressure-tight metal can having a valve-controlled opening. The aerosol container is then filled under pressure with the propellant and is ready for use.

In the following examples, which serve to illustrate the invention, parts and proportions are by weight and temperatures are in ° C.

EXAMPLE 1

| | Parts |
|---|---|
| Aluminum sulfamate (particulate, 10 to 25μ) | 3.50 |
| *Fumed colloidal silica (particulate, 1.1 to 5μ) | 0.35 |
| Propylene-1,2-dipelargonate (liquid) | 6.50 |
| Hexachlorophene (powder) | 0.10 |
| Perfume | 0.20 |
| Mixture of $CCl_3F$ and $CCl_2F_2$ in 60:40 ratio | 89.35 |

*Cab-O-Sil M5, manufactured by Cabot Corporation

The above constituents are mixed together and introduced into an aerosol container in the order given (the container is valved, pressure holding and normally closed) in accord with conventional aerosol formulation techniques. In use the aerosol composition is dispensed in a rapidly settling uniform spray which readily holds to the skin. When tested against prior art aerosol formulations using conventional ester emollient carriers the present composition very efficiently inhibits perspiration. In all instances, the present composition provides a well-adhering, smooth, dry film on the user's skin without the unpleasant oily sensation characteristic of the prior art aerosol antiperspirant compositions containing conventional esters as emollient-carriers, using conventional ½, 1 and 2-second dispensing bursts per axilla.

EXAMPLE 2

-continued

| | Parts |
|---|---|
| Aluminum sulfamate powder (10 to 25 microns diameter) | 3.0 |
| Propylene glycol dipelargonate | 1.5 |
| *Bentone 38 | 0.2 |
| Propylene carbonate | 0.06 |
| Perfume | 0.1 |
| Propellant (65:35 ratio mixture of Propellants 11 and 12) | 95.14 |

*Manufactured by NL Industries, Inc.

The aerosol suspension is prepared by first making a suspension concentrate. Said concentrate is prepared by blending the "Bentone" with the propylene glycol dipelargonate and the propylene carbonate (wetting agent). The mixture is vigorously mixed at a temperature of about 20° C. to form a gel. The aluminum sulfamate is then added along with a portion of the propellant and the perfume and the composition is mixed to form a homogeneous concentrate. The concentrate is then placed in a can, sealed with a suitable aerosol valve, and pressurized with the propellant. Finally, the aerosol container is shaken and a stable aerosol suspension thereby obtained. In use, the aerosol package provides a smooth, adherent film composition which is a pleasant feeling, dry deposit that very effectively reduces perspiration.

EXAMPLE 3

| | Parts |
|---|---|
| Aluminum chlorohydrate (particulate, 10 to 25μ) | 3.50 |
| *Fumed colloidal silica (particulate, 1.1 to 5μ) | 0.35 |
| Propylene-1,2-dipelargonate (liquid) | 6.50 |
| Hexachlorophene (powder) | 0.10 |
| Perfume | 0.20 |
| Mixture of $CCl_3F$ and $CCl_2F_2$ in 60:40 ratio | 89.35 |

*Cab-O-Sil M5, manufactured by Cabot Corporation

The above formula is prepared by mixing in the manner described with respect to Example 1 and in the preceding specification and the product made is utilized as an antiperspirant by spraying a dry film of the components onto the human skin. It is found to be an effective antiperspirant which leaves an adherent, smooth, dry non-oily film on the skin and does not cause any unpleasant oily sensation, such as that often observed after use of prior art formulations containing other emollient-carriers than those of the present compositions, at application rates of 0.1 to 2 grams per axilla, e.g. 0.5 and 1.0 g./axilla.

EXAMPLE 4

| | Parts |
|---|---|
| Aluminum chlorhydrate powder (10 to 25 microns diameter) | 3.0 |
| Propylene glycol dipelargonate | 1.5 |
| Bentone 38 | 0.2 |
| Propylene carbonate | 0.06 |
| Perfume | 0.1 |
| Propellant mixture (65:35 ratio of Propellants 11 and 12) | 95.14 |

The above formula is prepared by mixing in the manner described with respect to Example 2 and in the preceding specification and the product made is utilized as an antiperspirant by spraying a dry film of the components onto the human skin. It is found to be an effective antiperspirant which leaves an adherent, smooth, dry non-oily film on the skin and does not cause any unpleasant oily sensation.

EXAMPLE 5

|  | Parts |
|---|---|
| Aluminum chlorhydrate powder | 1.5 |
| Aluminum sulfamate powder | 1.5 |
| Propylene glycol dipelargonate | 1.5 |
| Bentone 38 | 0.2 |
| Propylene carbonate | 0.06 |
| Perfume | 0.1 |
| Propellant mixture (65:35 ratio of Propellants 11 and 12) | 95.14 |

EXAMPLE 6

|  | Parts |
|---|---|
| Aluminum chlorhydrate powder of average particle size of about 15 microns | 3.0 |
| Propylene glycol dipelargonate | 1.5 |
| Bentone 38 | 0.2 |
| Finely divided talc (0.5 to 40 microns, averaging about 15 microns diameter) | 1.4 |
| Propylene carbonate | 0.06 |
| Perfume | 0.10 |
| *Propellant (65:35 ratio mixture of Freons 11 and 12) | 93.74 |

*Manufactured by E.I. DuPont de Nemours & Company, Inc.

EXAMPLE 7

|  | Parts |
|---|---|
| Aluminum chlorhydrate powder of average particle size of about 15 microns | 3.0 |
| Propylene glycol dipelargonate | 4.0 |
| Cab-O-Sil M5 | 0.35 |
| Perfume | 0.1 |
| Propellant mixture (65:35 ratio of Propellants 11 and 12) | 92.55 |

EXAMPLE 8

|  | Parts |
|---|---|
| Aluminum chlorhydrate powder, finely divided | 3.0 |
| Propylene glycol dipelargonate | 6.5 |
| Bentone 38 | 0.4 |
| Propylene carbonate | 0.1 |
| Perfume | 0.2 |
| Propellant mixture (2:1 Propellants 11:12 ratio) | 89.8 |

EXAMPLE 9

|  | Parts |
|---|---|
| Aluminum chlorhydrate powder finely divided (10 to 25 microns diameter) | 3.0 |
| Propylene glycol dipelargonate | 4.0 |
| Bentone 38 | 0.2 |
| *Dry Flow starch | 1.0 |
| Propylene carbonate | 0.06 |
| Perfume | 0.2 |
| Propellant mixture (2:1 $CCl_3F:CCl_2F_2$ ratio) | 91.54 |

*National Starch and Chemical Corporation

The compositions described in Examples 5–9 are tested and the resulting compositions have good antiperspirant activity and produce adherent smooth- and dry-feeling coatings on the skin which do not cause the user to experience an unpleasant oily sensation such as is often otherwise felt utilizing prior art powder aerosol antiperspirant products which do not dust or fume excessively. The compositions settle quickly in air and do not produce a cloud of antiperspirant that could readily be inhaled by a careless user.

When various changes are made in the described formulas in accordance with the invention, satisfactory antiperspirant aerosol powder products are also made. Thus, when in any of the Examples the antiperspirant salt is replaced by aluminum chloride, aluminum sulfate, aluminum oxychloride, zirconium tetrachloride, zirconyl oxychloride or zinc sulfocarbolate, a product of essentially the same characteristics is produced except that the antiperspirant effect varies somewhat based upon the particular salt used. However, the powdered spray adheres satisfactorily to the skin, does not form a long term suspended cloud and is non-oily in both appearance and feel. To obtain the smooth coating of powder, particle sizes of any insoluble astringent are held within the 1 to 100 micron diameter range, e.g. 10, 20 and 35 microns.

In the Examples and in those formulas in which the aluminum chlorhydrate is replaced by other antiperspirants, when some or all of the propylene glycol dipelargonate contents are replaced with corresponding quantities of propylene-1,3-dipelargonate (the dipelargonate of the examples is the 1,2-isomer); propylene-1,2-dioctanoate; propylene-1,3-dioctanoate; propylene-1,2-didecanoate; propylene-1,3-didecanoate; ethylene-1,2-dipelargonate; ethylene-1-octanoate-2-pelargonate; ethylene-1,2-di-(2-ethylhexanoate); and butylene-1,2-dipelargonate, good antiperspirant products result which are non-oily to the skin. Also, when in any of the aforementioned examples or the modifications thereof the dispersing agent is changed, substituting in whole or in part talcs, natural clays, synthetic clays, insoluble soaps, starches or chemically modified starches as dispersing agents for that utilized in the formula, provided that a sufficient quantity of the dispersing agent is employed to maintain the antiperspirant dispersed in the propellant, good antiperspirant effects are obtained without production of a sticky or oily product. When employing starches in such applications normally from 1 to 3% thereof will be utilized, e.g. 1%, 1.5%, 2%, and when hydrophobic clays such as Bentone 38 are used instead the proportion thereof that is found to be satisfactory is preferably from 0.05 to 0.5%, e.g. 0.1%, 0.2%, 0.4%. Although insoluble and sometimes soluble soaps, such as aluminum stearate may be employed and although saturated monoalkanolamides are useful sticking agents and can help to disperse the antiperspirant compound in the propellant, care will be exercised in utilizing such materials to avoid employing so much as to produce an oily or sticky feeling on the skin. Preferably, such components will be only a minor proportion of the dispersing agent, e.g. 5–30% thereof.

The invention has been described with respect to illustrative and working examples thereof but is not to be considered as limited to these because it is evident that one of ordinary skill in the art, with the present application before him, will be able to utilize equivalents and substitutes for elements and process steps hereof without departing from the spirit of the invention or going beyond its scope.

What is claimed is:

1. A dry anhydrous aerosol antiperspirant composition in a valved, normally closed pressurized dispensing container which comprises 0.2 to 12% by weight of an astringent powder comprising at least one astringent, antiperspirant acid-reacting salt of a member of the group cohaving a particle size of less than about 100 microns 0.3 to 50% of Propylene-1,2-dipelargonate, and from about 60 to 98% of a non-toxic gas-forming liquid propellant.

2. A composition according to claim 1 in which the astringent salt is aluminum sulfamate.

3. A composition according to claim 1 and further containing about 0.05 to 3% of a suspending agent for the astringent powder.

4. A composition according to claim 3 in which the suspending agent is selected from the group consisting of hydrophobic clay, colloidal silica, aluminum soap, starch and talc.

5. A composition according to claim 4 wherein there is present 1 to 10% of the astringent powder, 0.3 to 12% of the propylene-1,2-dipelargonate, and 60 to 98% of propellant.

6. A composition according to claim 5 wherein the astringent salt is aluminum sulfamate, of which there is present 2.5 to 6%, and there is present 0.5 to 8% of the propylene-1,2-dipelargonate, 80 to 94% of the propellant, and 0.02 to 0.5% of an antibacterial agent.

7. A composition according to claim 1 wherein the astringent salt is aluminum chlorhydrate, and further containing colloidal silica or hydrophobic clay as suspending agent.

8. A composition according to claim 5 wherein the astringent salt is aluminum chlorhydrate, and the suspending agent is colloidal silica or hydrophobic clay.

9. A composition according to claim 6 wherein there is present about 3.5% of aluminum sulfamate, about 6.5% of propylene 1,2-dipelargonate, about 90% of propellant, and about 0.4% of fumed colloidal silica.

10. A method of counteracting production of human perspiration which comprises spraying onto the axillae a composition of claim 1 from the pressurized dispensing container thereof.

* * * * *